United States Patent [19]

Cartmell

[11] Patent Number: 4,543,958

[45] Date of Patent: Oct. 1, 1985

[54] MEDICAL ELECTRODE ASSEMBLY
[75] Inventor: James V. Cartmell, Dayton, Ohio
[73] Assignee: NDM Corporation, Dayton, Ohio
[21] Appl. No.: 447,423
[22] Filed: Dec. 6, 1982

Related U.S. Application Data

[63] Continuation-in-part of Ser. No. 246,873, Mar. 23, 1981, , which is a continuation-in-part of Ser. No. 34,394, Apr. 30, 1979, Pat. No. 4,257,424.

[51] Int. Cl.[4] .......................... A61B 5/04; A61N 1/04
[52] U.S. Cl. .................................. 128/640; 128/798; 128/803
[58] Field of Search .............................. 128/639–641, 128/644, 783, 798, 802, 803, 303.13; 174/117 A

[56] References Cited

U.S. PATENT DOCUMENTS

| | | | |
|---|---|---|---|
| 1,959,293 | 5/1934 | Phillips | 164/42 |
| 1,973,911 | 9/1934 | Ruben . | |
| 2,230,829 | 2/1941 | Cesareo | 312/91 |
| 2,417,497 | 3/1947 | Hulslander | 206/58 |
| 2,808,352 | 10/1957 | Coleman et al. | 117/227 |
| 2,943,628 | 7/1960 | Howell | 128/418 |
| 3,101,282 | 8/1963 | Glassco et al. | 118/40 |
| 3,132,204 | 5/1964 | Giellerup | 174/117 |
| 3,173,728 | 3/1965 | Sheer | 312/73 |
| 3,283,886 | 11/1966 | Addis et al. | 206/52 |
| 3,357,930 | 12/1967 | Marks et al. | 252/518 |
| 3,368,522 | 2/1968 | Cordis | 118/43 |
| 3,435,127 | 3/1969 | Rose et al. | 174/94 |
| 3,475,213 | 10/1969 | Stow | 117/227 |
| 3,505,144 | 4/1970 | Kilduff et al. | 156/259 |
| 3,547,105 | 12/1970 | Paine | 128/2.06 |
| 3,607,788 | 9/1971 | Adolph | 252/510 |
| 3,640,741 | 2/1972 | Etes | 106/170 |
| 3,662,745 | 5/1972 | Cosentino | 128/2 E |
| 3,674,176 | 7/1972 | Sagi | 221/135 |
| 3,746,004 | 7/1973 | Jankelson | 128/410 |
| 3,752,303 | 8/1973 | Foster | 206/52 R |
| 3,762,946 | 10/1973 | Stow | 117/227 |
| 3,805,769 | 4/1974 | Sessions | 128/2.06 E |
| 3,828,766 | 8/1974 | Krasnow | 128/2.1 E |
| 3,832,598 | 8/1974 | Oehmke et al. | 174/117 A |
| 3,835,992 | 9/1974 | Adams | 206/390 |
| 3,961,623 | 6/1976 | Milani | 128/2.06 E |
| 3,976,055 | 8/1976 | Monter et al. | 128/2.06 E |
| 3,993,049 | 11/1976 | Kater | 128/2.06 E |
| 3,998,215 | 12/1976 | Anderson et al. | 128/2.06 E |
| 4,016,869 | 4/1977 | Reichenberger | 128/2.1 E |
| 4,026,757 | 5/1977 | Crawford | 156/575 |
| 4,063,352 | 12/1977 | Bevilacqua | 29/630 |
| 4,066,078 | 1/1978 | Berg | 128/2.06 E |
| 4,067,342 | 1/1978 | Burton | 128/418 |
| 4,141,366 | 2/1979 | Cross et al. | 128/418 |
| 4,155,354 | 5/1979 | Rasmussen | 128/640 |
| 4,166,453 | 9/1979 | McClelland | 128/639 |
| 4,257,424 | 3/1981 | Cartmell | 128/641 |
| 4,267,840 | 5/1981 | Lazar et al. | 128/303.17 |
| 4,273,135 | 6/1981 | Larimore et al. | 128/640 |
| 4,274,420 | 6/1981 | Hymes | 128/641 |
| 4,365,634 | 12/1982 | Bare et al. | 128/640 |
| 4,367,745 | 1/1983 | Welage | 128/303.13 |
| 4,419,091 | 12/1983 | Behl et al. | 128/803 X |

FOREIGN PATENT DOCUMENTS

| | | | |
|---|---|---|---|
| 2271846 | 12/1975 | France | 128/803 |
| 6803290 | 9/1968 | Netherlands . | |
| 1499801 | 2/1978 | United Kingdom . | |

Primary Examiner—Lee S. Cohen
Attorney, Agent, or Firm—Dybvig & Dybvig

[57] ABSTRACT

Dispensable medical electrodes formed as separable segments of an indefinitely long substrate are formed by applying to the substrate a longitudinally extending stripe of a conductive paint and by overlaying the painted stripe at periodic intervals corresponding to the separable segments with films of a conductive adhesive material which films generally traverse the width of the substrate.

After conditioning the conductive adhesive films to a desired moisture content, the substrate is rolled spirally upon itself and stored in an electrode dispenser device. Two types of dispenser device are disclosed. In one type, the dispenser confines a humidity control solution which maintains substantially constant the moisture content of the conductive adhesive films. The second type of dispenser device confines an activating solution which is applied to the conductive adhesive films located on the electrode segments as the electrode segments are dispensed.

8 Claims, 9 Drawing Figures

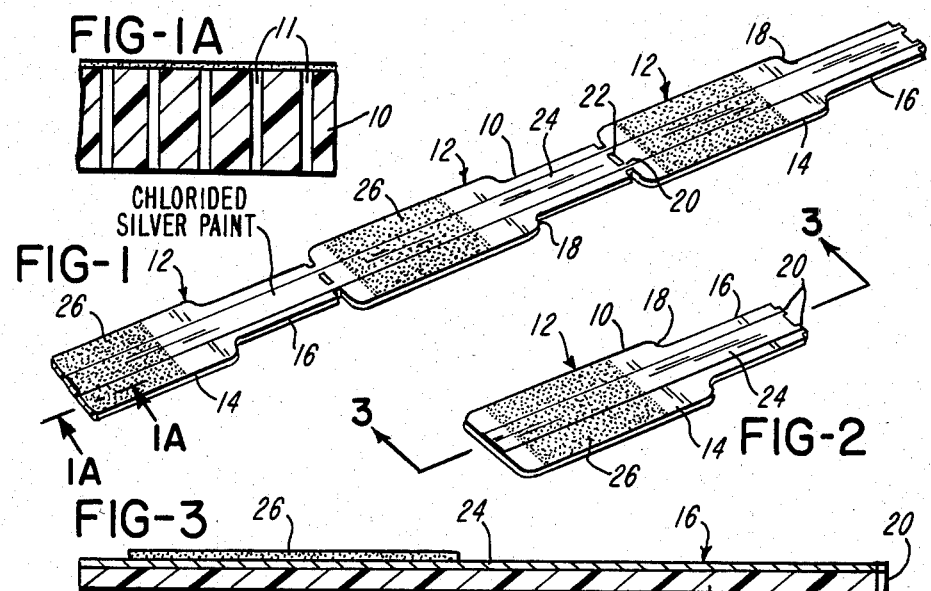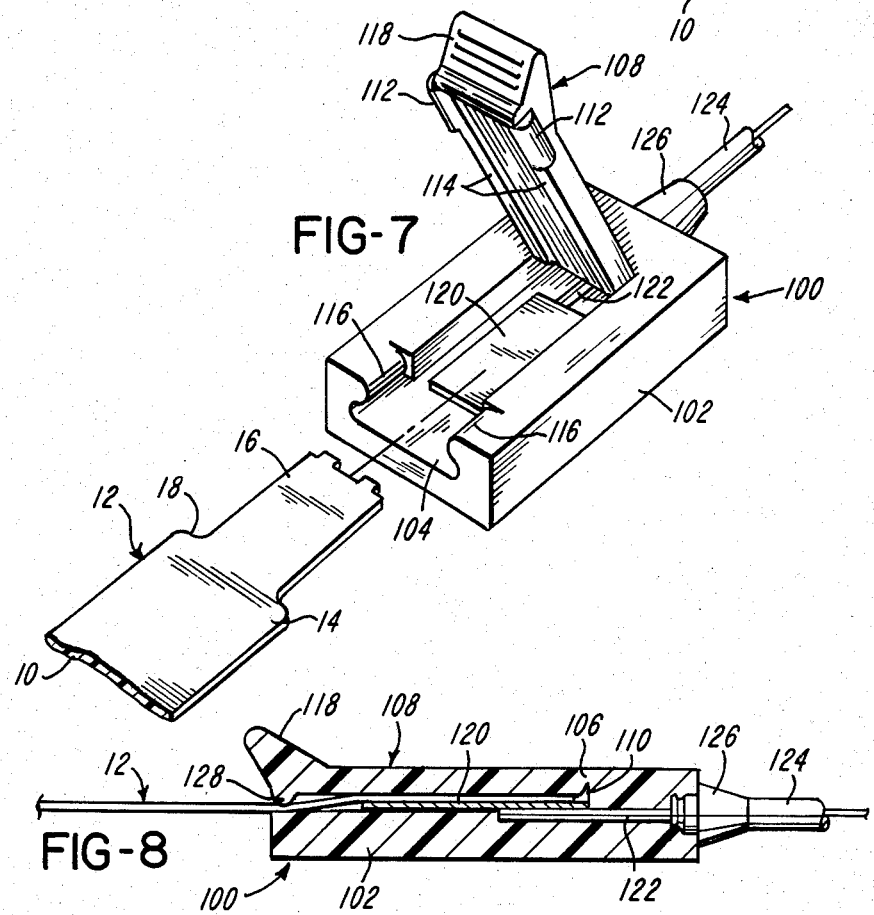

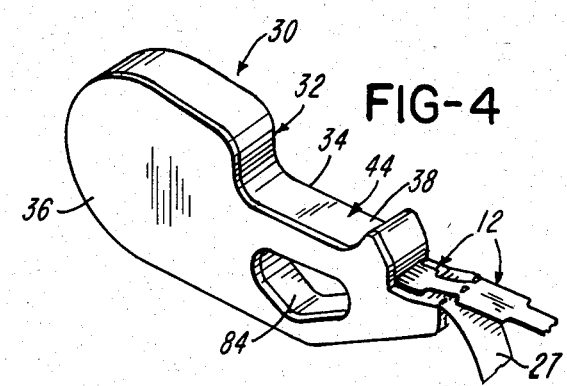
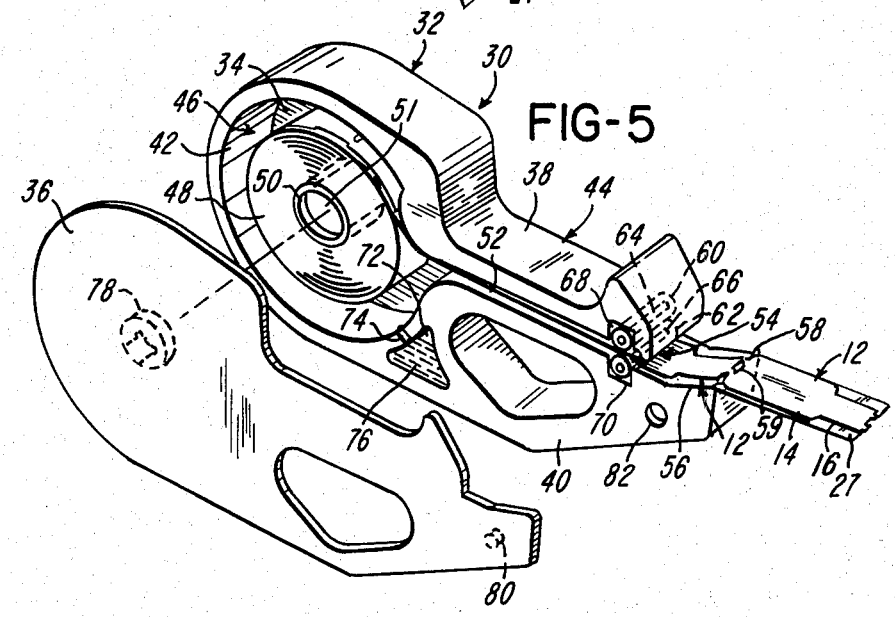
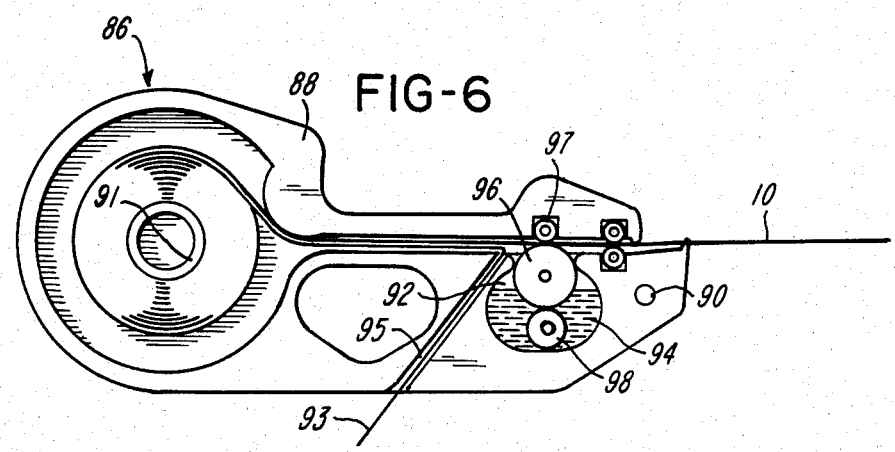

MEDICAL ELECTRODE ASSEMBLY

This application is a continuation-in-part of pending application Ser. No. 246,873, filed Mar. 23, 1981, which is a continuation-in-part of application Ser. No. 34,394 filed Apr. 30, 1979, now U.S. Pat. No. 4,257,424 issued Mar. 24, 1981.

SUMMARY OF THE INVENTION

It is known in the prior art to produce highly efficient yet inexpensive medical electrodes by applying a layer or stripe of conductive paint such as a silver paint to a nonconductive plastic substrate, one portion of the paint layer being bridged to the skin of a subject under examination, such as a patient, by means of an electrolyte layer or sponge and another portion of the conductive paint remaining exposed for connection to peripheral equipment such as monitoring equipment, stimulating equipment or the like.

In the present invention, a stripe of conductive paint is applied to a substrate comprising integrally formed electrode segments partially separated by weakenings which allow individual electrode segments or groups of electrode segments to be severed from a larger supply. For convenient dispensing of the electrodes from the larger supply, the supply is stored as a roll of connected electrode segments in a protective housing or conditioner having a slot through which conditioned electrode segments may be sequentially removed.

In one embodiment, the protective housing confines a humidifying solution which moisturizes an atmosphere delivered through a ventilation opening to the electrode segments stored in the housing which are thereby provided with a sufficient moisture or humidity to preserve the tackiness and electrical conductivity of a polymeric film tailored to perform at such humidity as both an adhesive and an electrolyte, the humidified electrode segments being directly attachable to the skin of a subject without further preparation.

In another embodiment, the electrode conditioner carries in it a supply of activating fluid and a fluid application means which activates the electrode segments as they are removed, thus relieving the requirement for a controlled humidity environment.

BRIEF DESCRIPTION OF THE DRAWINGS

In the drawings:

FIG. 1 is a fragmentary perspective view of a strip of integrally connected medical electrodes in accordance with the present invention.

FIG. 1A is a greatly enlarged fragmentary section illustration taken along the line 1A—1A through the thickness of a portion of the strip of FIG. 1, where coated by a conductive adhesive composition.

FIG. 2 is a perspective view of a single medical electrode in accordance with this invention.

FIG. 3 is a cross-sectional view with exaggerated thickness taken substantially along the line 3—3 of FIG. 2.

FIG. 4 is a perspective view of a first embodiment of an electrode conditioner in accordance with the present invention, this figure illustrating a portion of a strip of electrodes and adjacent release paper projecting out of an exit opening of the conditioner.

FIG. 5 is an enlarged, partly exploded perspective view of the conditioner of FIG. 4.

FIG. 6 is a side elevational view of a portion of a second embodiment of an electrode conditioner in accordance with this invention.

FIG. 7 is a partly exploded fragmentary perspective illustration of a medical electrode of this invention and a cable connector for electrically connecting the electrode to peripheral equipment.

FIG. 8 is a longitudinal cross-sectional view of the cable conductor of FIG. 7 with the electrode connected thereto.

DETAILED DESCRIPTION

Referring to the drawings in greater detail, FIGS. 1, 1A, 2 and 3 illustrate a nonconductive substrate 10 which was initially an indefinitely long strip of uniform width and thickness. In the preferred embodiment of this invention, the substrate comprises a flexible and dimensionally stable sheet of plastic material such as polyethylene terephthalate which may have a thickness in the range of ½ mil (0.00127 cm) to 20 mils (0.0508 cm). Such substrate is sold under the trademark Mylar by the DuPont Chemical Corporation. As shown, the substrate has been shaped by suitable cutting dies so as to comprise an indefinite number of electrodes 12 each having a broad heel section 14 and a relatively narrow toe section 16, each electrode 12 having sloping shoulders 18 in the opposite side margins thereof where the side-to-side width of the electrodes is reduced from the width of the heel section 14 to the width of the toe section 16. The toe section of each of the electrodes 12 is integrally attached to the heel section of the next adjacent electrode 12 by a pair of webs 20 that are left intact as a part of the substrate 10 when perforations 22 are formed in the body of the substrate between the webs 20. The webs 20 thus preserve the integrity of the substrate 10 between adjacent electrodes 12 but provide only a weak connection between adjacent electrodes 12 such that the adjacent electrodes can be separated with relative ease.

Disposed centrally between the sides of the substrate 10 and extending longitudinally along the entire length of one face of the substrate is a stripe 24 of an electrically conductive paint which preferably comprises a plastic carrier loaded with metallic particles or flakes. A commercially available example of such paint is Du-Pont conductor composition No. 9793 available from the DuPont Chemical Corporation. For the purposes of this invention there is admixed to this commercially available paint a small quantity of silver chloride powder which will cause the stripe 24 to behave as a chlorided silver paint conductor. Alternatively, the chloriding can be induced by application to the paint in the presence of an electrolyte of an electrical chloriding current or by other techniques known in the art.

In the utilization of the present invention, the heel section 14 will be affixed to the skin of the subject or patient for purposes of exchanging electrical signals between the skin of the patient and the peripheral equipment. To allow an adequate transpiration to take place, the heel section is perforated as will be described.

Thus, the heel sections are perforated uniformly throughout by punching and/or melting to produce pores 11 extending through the thickness of the substrate in the heel sections 14. The pores 11 may be confined to the heel sections 14. However, it is also possible to distribute the pores 11 throughout the major surfaces of the substrate 10. By confining the pores 11 to the heel sections 14, however, irregularities at the side margins may be avoided and the tearing designed to occur between the heel sections 14 and the toe sections 16 of adjacent electrodes confined to weaknesses created by the perforations 22. Thus, it is possible to so distribute the pores 11 that these pores do not in themselves create weaknesses along which the substrate will tend to tear. Where indiscriminate tearing of the substrate poses no problem, the pores 11 may be distributed uniformly over the major areas of the substrate 10. Whether the pores 11 are distributed uniformly throughout the major areas of the substrate or confined to selected areas such as the heel sections 14, the pores, which may be approximately one-sixteenth of an inch in diameter ( 0.158 cm), may occupy approximately 50 percent of the surface area of the substrate 10 in those areas where the pores 11 are provided. The pores may be arranged in any pattern desired, examples being pores aligned in parallel rows or, if desired, pores aligned in rows with the pores in one row staggered with respect to pores in adjacent rows. The perforations 22 may be formed simultaneously as the pores 11 are formed. Referring to FIG. 1A pores 11 extending through the thickness of the substrate 10 are illustrated. In the preferred practice, the stripe 24 is applied to the substrate 10 after formation of the pores 11 and any of various screening techniques is employed to minimize loss of the paint through the pores 11 and perforations 22.

Traversing each of the heel sections 14 is a film 26 of a conductive adhesive which overlies the stripe 24 and extends laterally beyond the side edges of the stripe 24 to fully cross the width of the heel section 14.

In the preferred embodiment, the conductive adhesive may be applied to the substrate 10 before the side edges of the substrate have been cut to shape but may alternately be applied thereafter. In any event, it is preferred to apply the conductive adhesive film 26 after perforating the heel portions 14 so as to form the pores 11.

In one version, the conductive adhesive film 26 comprises a naturally occurring karaya gum which has blended therein an electrolyte which is derived from an aqueous salt solution. Such composition is available in sheet form from Lectec Corporation, 120 South Crosstown Circle, Eden Prairie, Minn. Various other conductive adhesive compositions could be used. Suitable compositions are described, for example, in the following United States Patents: Marks et al., U.S. Pat. No. 3,357,930; Kater U.S. Pat. No. 3,993,049; Berg U.S. Pat. No. 4,066,078; and Cross et al., U.S. Pat. No. 4,141,366. Those familiar with the art will appreciate that the formulation of the composition will depend on the desired use of the electrode, i.e. whether for monitoring or stimulation.

In the preferred embodiment, the conductive adhesive comprises a synthetic polymer which is preferably a hydrophilic polymer blended with an aqueous electrolyte. A water based emulsion including an acrylic resin and a suitable plasticizer is the polymer of choice. The electrolyte of choice is sodium chloride. The blended polymer and aqueous electrolyte are applied to the substrate as a thin film which is then dried by heating, the dried film preferably having a thickness in the range of 1 mil (0.00254 cm) to 4 mils (0.01016 cm).

In the practice of the present invention, the conductive adhesive, whether based on natural or synthetic resins, gums and the like, is tailored by known techniques to have a good ionic conductivity and adequate tackiness when equilibrated with an atmosphere whose relative humidity is in the range of approximate 30 percent relative humidity to approximately 60 percent relative humidity. This humidity range is found to be suitable for processing purposes. However, those skilled in the art will appreciate that both the ionic conductivity and tackiness can be satisfactory at substantially different humidity levels. The 30 to 60 percent range is preferred because in this range there is less of a tendency of the conductive adhesive flim 26 to transfer to the skin of a patient. Thus, within the indicated humidity range the conductive adhesive film 26 will tend to stay with the electrode and separate cleanly from the skin of the patient when the electrode is removed. As will be described hereafter, the substrate 10 containing the electrodes 12 will be wound for storage in a conditioner and since such storage may occur over long periods of time, it is preferable to employ a release means such as a release paper 27 interleaved with the wound substrate. Alternatively a coating, not shown, of a release agent such as silicone or the like may be applied to that surface of the substrate 10 which is opposite the surface supporting the conductive adhesive films 26.

Those skilled in the art will recognize that each of the electrodes 12, prepared as described, contains the basic ingredients for a medical electrode such as may be employed in electrocardiograph monitoring. Thus, each electrode 12 comprises, as best shown in FIGS. 2 and 3, a substrate 10, an electrical conductor (the stripe 24) which is exposed at the toe section 16 for connection to peripheral instrumentation such as an electrocardiograph monitor, and an electrolyte (dispersed throughout the conductive adhesive film 26, such adhesive having been applied to the heel section 14 of the electrode 12). In the humidified condition above described, i.e. 30 percent to 60 percent relative humidity, the conductive adhesive has an adequate tackiness for attachment of the conductive adhesive film 26 to the skin of a subject and also has an adequate signal transmission capability for transmitting electrical signals between the skin and the conductive stripe 24 to operate as a medical electrode. What is required, however, is a means to sustain such electrode qualities during storage and shipment or, in the alternative, to restore such qualities at the time the electrode is to be used.

FIGS. 4 and 5 illustrate a conditioner generally designated 30 including means to activate or sustain the activation of electrodes to be dispensed or removed in accordance with the present invention. The conditioner 30 comprises a molded plastic housing generally designated 32 having, as viewed in FIGS. 4 and 5, a far side wall 34 and a near side wall 36. Spanning between the side walls 34 and 36 are housing body portions comprising a top housing portion 38 and a bottom housing portion 40 which integrally join with an arcuate rear wall 42. As shown in FIG. 5, the far side wall 34, the top housing portion 38, the bottom housing portion 40 and the rear wall 42 are all integrally formed in one piece, preferably of molded plastic that for convenience is referred to herein as a housing body member 44. The near side wall 36 prior to assembly of the conditioner is formed as a separate plate which, as a final step in the assembly of the conditioner 30, is permanently affixed to the housing body member 44 as will be described below.

The housing body member 44 is shaped to provide a generally cylindrical chamber 46 sized to receive a roll 48 of electrodes 12 connected as shown in FIG. 1 and wound on a hollow roller 50, mounted on an axle 51 which may be molded with and affixed to the far side wall 34 of the housing body member 44. A strip passageway 52 extends longitudinally of the housing body member 44 from the roll chamber 46 to an exit opening 54 at the front end of the dispenser located generally between the forwardmost end of the top housing portion 38 and the confronting surface of the bottom housing portion 40. The bottom housing portion 40 further includes a forwardly extending ledge 56 terminating at its forwardmost end with a separation edge 58 aligned generally with the exit opening 54 and provided with one or more teeth 59 for interfitting the perforations 22 between electrodes 12. Preferably the serially connected electrodes 12 are so wound to form the roll 48 that their toe sections 16 are all on the clockwise side of their heel sections 14 and the substrate 10 winds in the clockwise sense from its innermost convolution to its outermost convolution. Accordingly, one may engage the toe portion of an electrode lying on the ledge 56 and pull the electrode out of the conditioner 30 until the perforation 22 is engaged by the tooth 59 of the separation edge 58 without touching the conductive adhesive 26. As is apparent, the electrode 12 which has been fully pulled out of the conditioner 30 may be readily severed by pulling downwardly on the toe portion 16 to cause the webs 20 connected to the next adjacent electrode 12 to be severed. In those cases where a release paper 27 such as is shown in FIGS. 4 and 5 lies adjacent the electrodes 12, this release paper is also perforated in alignment with the perforations 22 so as to be torn away over the separation edge 58 along with the adjacent electrode or electrodes 12. The release paper is then readily separated by the nurse or attendant from the severed electrodes. The toe portion 16 of the adjacent and unsevered electrode 12 will then lie on the ledge 56 in a position convenient for its removal at a later time.

A pair of nip rollers comprising an upper roller 60 and a lower roller 62 are rotatably mounted on axles 64 and 66 respectively that may also be molded integrally with the far side wall 34 as part of the housing body member 44. The nip rollers 60 and 62 preferably are made from rubber or other resilient material and are so located with respect to one another that electrodes 12 and any adjacent release paper are squeezed therebetween as they are pulled from the conditioner 30. The surfaces of the nip rollers 60 and 62 accordingly meet on a line extending transversely through the center of the strip passageway 52. The nip rollers 60 and 62 are received within confronting sockets 68 and 70 in the housing top portion 38 and the housing body bottom portion 40 respectively of a size and shape to permit the nip rollers 60 and 62 to rotate but to lightly engage them and therefore substantially preclude an interchange between the atmosphere inside the conditioner 30 and the atmosphere outside the conditioner 30.

Disposed within the conditioner 30 is a compartment 72 having atmospheric communication to the chamber 46 through one or more vent passageways 74. The compartment 72 is partly filled by a constant humidity solution 76 formed from distilled water to which has been charged a suitable salt. The constant humidity solution 76 is selected using techniques well-known to those concerned with humidified atmospheres to maintain the air within the conditioner 30 at a substantially constant relative humidity at room temperatures in the range of 30 to 60 percent relative humidity, this being the relative humidity range discussed above for causing the conductive adhesive film 26 to be adequately tacky for adhesive attachment to the skin of the subject and also to serve as an acceptable electrolyte.

During assembly of the conditioner 30 after the vent passageway or passageways 74 have been formed such as with the assistance of suitable drills or cutters, the nip rollers 60 and 62 may be mounted on the axles 64 and 66 and the electrode roll 48, the electrodes 12 of which, together with any adjacent release paper, are already equilibrated with a 30 to 60 percent relative humidity atmosphere, mounted on the hollow roller 50 surrounding the axle 51 and threaded through the strip passageway 52 so that the toe section 16 of the free end of the strip of electrodes overlies the ledge 56. The constant humidity solution can then be poured into the compartment 72, with the housing body 44 resting on a horizontal table. The plate forming the side wall 36 is then fitted over the housing body member 44. For this purpose it may have a stub axle 78 adapted to fit within the roller 50 and a pin 80 adapted to fit within an aperture 82 formed in the confronting face of the housing body member 44. The aperture 82 may desirably be provided with a bead or the like which receives the pin 80 with a snug fit. The stub axle 78 may likewise be snap fittedly received within the hollow roller 50. The side plate member is also preferably secured to the body member 44 by a hot melt or other adhesive to ensure that there is no interchange of air between the inside and the outside of the conditioner 30 and also to securely trap the constant humidity solution 76 within the compartment 72.

In the use of the conditioner 30, electrodes are drawn out of the exit opening 54 one at a time or in groups of two or more electrodes, as needed. Since, as described, the electrodes have been preconditioned before insertion into the conditioner 30 and can remain so conditioned for long periods while remaining in the conditioner 30, all electrodes removed from the conditioner 30 are ready for immediate application to the skin of a subject to be monitored or stimulated.

The dispenser ledge 56 with its tooth 59 is so spaced with respect to the nip rollers 60 and 62 that when the toe of one electrode 12 and any adjacent release paper rests on the ledge 56 to engage the tooth 59, the portion of its heel section coated by the adhesive film 26 and any adjacent release paper remains on the opposite side of the nip rollers 60 and 62. This means, for example, that on a given day one or more electrodes 12 can be removed from the conditioner and then on a following day, for example, the next electrode to be used, whose toe section is already projecting out of the exit opening, can be removed for use without its adhesive film 26 having lost its humidity conditioned state. This necessarily requires that the toe section and the uncoated portion of the heel section of each electrode and corresponding release paper be longer in longitudinal extension than the separation between the seal formed by the nip rollers 60 and 62 and the separation edge 58. As a convenience for gripping the conditioner 30, a through bore 84 extends through the lower housing portion 40. The bottom surface of the conditioner is preferably flat so that the conditioner will remain upright when placed on a horizontal surface.

Although the indicated size and shape of the conditioner 30 is unimportant to this invention, it is presently preferred that it be sized so as to be conveniently held in one hand to permit the tearing away of an electrode 12 and any adjacent release paper by the other hand. The modified conditioner 86 of FIG. 6 is similar in external appearance to the preferred embodiment of FIGS. 4 and 5, comprising a body member 88 similar to the housing body member 44 of FIGS. 4 and 5, and a sidewall plate (not shown) that may be similar to the previously described side wall 36 with adjustments having been made so that the side wall employed in the embodiment of FIG. 6 will have a pin such as the pin 80 appearing in FIG. 5 and will also have a stub axle such as the axle 78 appearing in FIG. 5 for engaging in the aperture 90 and in the roller 91 appearing in FIG. 6 so as to confine the various rollers exposed in FIG. 6, said side plate being secured to the body member 88 by a hot melt adhesive or the like not shown. What is different in the modification is that the compartment 72 which contained the constant humidity solution described in connection with the preferred embodiment has been eliminated and instead, near the exit end of the conditioner, there has been provided a solution chamber 92 which receives an activating solution 94. A cylindrical wiper roller 96 biased downwardly into the solution chamber 92 by a pressure roller 97 is frictionally rotated by the electrode segments which pass successively between the pressure roller 97 and the wiper roller 96, the wiper roller 96 being wetted by the fluid 94 as the wiper roller 96 rotates. The fluid wetting the roller 96 is carried upwardly as the roller rotates in the clockwise direction as viewed in FIG. 6 and partially transferred to that face of the electrode segment which is frictionally engaging and rotating the wiper roller 96.

It being desired that the faces of the electrode segments 12 to which the fluid 94 is transferred be the faces coated by the conductive adhesive film 26, the substrate 10 when wound for insertion into the conditioner of FIG. 4 is wound in a clockwise sense with the surface of the substrate 10 which bears the stripe 24 being curved concavely by the winding operation.

To increase the volume of fluid that may be transferred upwardly to the electrode segments 12, a second wetting roller 98 may be rotatably mounted in the chamber 92 below the first wiper roller 96. This second roller 98 is effective to continue the upward transfer of fluid to the electrode segments 12 even after the level of the fluid 94 in the chamber 92 is too low for direct wetting of the wiper roller 96.

While the drawings illustrate transfer rollers for conveying liquid from the chamber 92 to the confronting faces of the electrode segments 12, it will be appreciated that other devices such as capillary wicks and brushes are also suitable for this purpose.

In simplest form, the activating solution may be water which saturates the conductive adhesive contained in the film 26, so as to provide a surface which is tacky and which is also loaded with ions and thus is an effective electrolyte.

Referring to both of the conditioner mechanisms disclosed in FIGS. 4, 5 and 6, it can be appreciated that these conditioner mechanisms can be characterized as conditioners having included therein a preparation means which prepares the conductive adhesive films 26 for attachment to the skin of a patient. In the embodiment of FIGS. 4 and 5, the preparation means comprises the solution compartment 72 together with its constant humidity solution 76 and with the nip rollers 60 and 62 which, in combination assures that the already conditioned adhesive films 26 remain sufficiently tacky and conductive for immediate use.

In the embodiment of FIG. 6, the preparation means comprises the solution chamber 92 together with its associated means for conveying the activating solution from its chamber 92 to the films 26 which pass successively over the chamber 92, this preparation means assuring that the conductive adhesive films 26, although they may have experienced some dry out during storage and shipment, will be adequately moist when applied to the skin of a subject to possess both a sufficient tackiness and a sufficient conductivity for accomplishing the monitoring or stimulating function.

In the embodiment of FIG. 6, it is desirable that a release paper 93 be rolled with the substrate 10 and this release paper is separated from the substrate 10 by means of a drop channel 95 molded into the body member 88 of the modified conditioner 86. The drop channel 95 is shaped at its mouth with a sharp edge which separates the release paper from the substrate 10 in advance of the wiper roller 96 so that the release paper will not block the wiping action of this roller. The release paper is, of course, tailored to separate readily from the substrate 10 and drops freely through the drop channel 95. The presence of the drop channel means that some moisture may escape from electrodes stored in the conditioner. However, the presence of the wiper roller 96 and the activating solution applied thereby to the electrodes assures in any event that the electrodes will be adequately conditioned for application to the skin of a patient when removed from the modified conditioner 86.

While the present invention has been described with reference primarily to the accomplishment of patient stimulation and signal monitoring functions, those skilled in the art will appreciate that the most immediate function accomplished with the present invention is the dispensing of electrodes readily attachable to the skin of a subject. If the toe section of the electrode is then attached to signal monitoring equipment, the electrode functions as a monitoring electrode. If the toe section is attached to a source of voltage for stimulation purposes, then the electrode functions as a stimulation electrode.

Referring to the cable connector 100 appearing in FIGS. 7 and 8, the cable connector comprises a plastic tray 102 having a longitudinally extending channel 104 formed in the upper face thereof. Integrally formed at the upper surface of the tray 102 is a hinge 106 which is one-piece with a cover member 108, the cover member 108 being rendered pivotal on the hinge 106 by the molding of a notch 110 lying under the hinge 106 as shown in FIG. 8.

The cover 108 is molded with outwardly projecting latches 112 which are formed integrally on stiffening ribs 114 extending along the opposite sides of the cover member 108. The tray 102 is formed with inwardly projecting latch retainers 116 which are sized and shaped to receive and then seize the latches 112 as the cover member 108 is pivoted downwardly to press the latches 112 into interfitting engagement with the latch retainers 116.

The cover member 108 is provided with an outwardly sloped lifting grip 118 to allow an operator to lift the cover member 108 against the seizing grip of the latch retainers 116 at times when it is desirable to lift the cover member 108 to the position shown in FIG. 7.

When the cover member is lifted, as shown, there is exposed in the channel 104 a rectangular metal plate 120 from which extends an integrally connected conductor 122. This conductor 122 extends rearwardly from the plate 120 through the rearward end of the tray 102 where the conductor is surrounded by an insulator 124 received in a protective sleeve 126 molded integrally to the tray 102. FIGS. 7 and 8 show the conductor 122 and the insulator 124 as having been broken off or otherwise terminated near the rear end of the tray 102. In actual practice, however, the conductor 122 and the surrounding insulator 124 may be indefinitely long, the purpose being to effect an electrical connection between the metal plate 120 and peripheral equipment such as a source of stimulating voltage or electrical monitoring apparatus. As evident in FIG. 7, the channel 104 is sized to receive the toe section 16 of any one of the electrode segments 12 but is too small in dimension to accept any of the heel sections 14. Thus, an operator may insert any one of the toe sections 16 into the channel 104 without difficulty and, with closure of the cover member 108, the exposed conductive stripe 24 extending along the toe section 16 will be pressed into intimate engagement with the metal plate 120. As the cover member 108 is closed, a rib 128 formed integrally on the lifting grip 118 seizingly engages the root of the toe section immediately adjacent the heel section 14.

The heel section 14 thus remains outside the tray 102 where it can be conveniently attached by means of the conductive adhesive layer 26 to the skin of a patient with the seizing engagement of the rib 128 against the root of the toe section 16 being effective to support the weight of the tray 102 and any dangling conductor 122 as the adhesive film 26 adheres to the skin of a patient.

When the conductive adhesive layer 26 has been appropriately conditioned either by the humidified environment of the conditioner 30, or by the activating solution of the modified conditioner 86, the electrode segments are immediately attachable to the skin. The conditioned electrode, when contacted to the metal plate 120 upon insertion into the cable connector 100, is immediately operative for its intended purpose whether for electrode monitoring or patient stimulation.

Although the preferred embodiments of the present invention have been described, it will be understood that various changes may be made within the scope of the appended claims. Having thus described my invention, I claim:

1. An assembly of medical electrodes comprising an extended sheet of dimensionally stable nonconductive substrate material, a stripe of conductive paint adhered to one side of said extended sheet and extending the length of said sheet, said sheet having a plurality of weakened portions spaced apart to define segments along the length of said sheet, the segments of said sheet occupying the spaces between said weakened portions including a broad heel section proximal one end of each segment and a narrow toe section proximal the other end of each segment, each said segment traversed by a film of electrolyte including conductive adhesive lying over said stripe, and lying over only said broad heel section.

2. The electrode assembly of claim 1 wherein said heel section is penetrated by a plurality of pores.

3. The electrode assembly of claim 1 wherein said weakened portions comprise perforations through said substrate.

4. The electrode assembly of claim 1 wherein said substrate winds spirally about itself.

5. An assembly of medical electrodes comprising an extended sheet of dimensionally stable nonconductive substrate material, a stripe of conductive paint adhered to one side of said extended sheet and extending the length of said sheet, said sheet having a plurality of weakened portions spaced apart to define segments along the length of said sheet, the segments of said sheet occupying the spaces between said weakened portions each traversed by a film of conductive adhesive lying over said stripe, wherein each of the segments of said sheet occupying the spaces between said weakened portions includes a broad heel section proximal one end of each segment and underlying said film of conductive adhesive and a narrow toe section proximal the other end of each segment and not underlying said film of conductive adhesive.

6. The electrode assembly of claim 5 wherein said heel section is penetrated by a plurality of pores.

7. The electrode assembly of claim 5 wherein said weakened portions comprise perforations through said substrate.

8. The electrode assembly of claim 5 wherein said substrate winds spirally about itself.

* * * * *